United States Patent [19]

aus der Fünten et al.

[11] Patent Number: 4,528,385
[45] Date of Patent: Jul. 9, 1985

[54] METHOD OF PREPARING PHTHALIDE

[75] Inventors: Helmut aus der Fünten, Niederkassel-Mondorf; Wilhelm Vogt, Cologne, both of Fed. Rep. of Germany

[73] Assignee: Dynamit Nobel AG, Troisdorf, Fed. Rep. of Germany

[21] Appl. No.: 459,018

[22] Filed: Jan. 18, 1983

[30] Foreign Application Priority Data

Jan. 18, 1982 [DE] Fed. Rep. of Germany ....... 3201300

[51] Int. Cl.³ ........................................... C07D 307/88
[52] U.S. Cl. .................................................. 549/307
[58] Field of Search ........................................ 549/307

[56] References Cited

U.S. PATENT DOCUMENTS 2,079,325  5/1937  Larchar ............................... 549/307
2,114,696  4/1938  Austin et al. ........................ 549/307

Primary Examiner—Jane T. Fan
Attorney, Agent, or Firm—Felfe & Lynch

[57] ABSTRACT

The present invention relates to the hydrogenation of phthalic acid anhydride to phthalide. A nickel catalyst of low nickel content is used as hydrogenation catalyst, and a benzoic acid alkyl ester as solvent. Small amounts of an alkanol can be added to the benzoic acid ester. On the basis of these specific conditions, the formation of by-products such as toluylic or phthalic acids in the hydrogenation is greatly diminished, and phthalide yields are obtained which, if the preferred conditions are maintained, can amount to as much as 90%.

12 Claims, No Drawings

METHOD OF PREPARING PHTHALIDE

BACKGROUND OF THE INVENTION

The subject matter of the present invention is a method of preparing phthalide by the catalytic hydrogenation of phthalic acid anhydride with the aid of a nickel catalyst fixed on a support material.

The catalytic hydrogenation of phthalic acid anhydride in the presence of nickel or platinum catalysts in various solvents is known (cf. Houben-Weyl, "Methoden der organischen Chemie", 6/2, (1963), pp 732 to 733). The yields in these known methods amount to 75% at most, depending on the solvent and catalyst used. For example, when Raney nickel is used in absolute ethanol at a hydrogen gas pressure of 165 bar at 160° C. reaction temperature, phthalide yields of 73% are obtained; when acetic acid butyl ester is used as solvent, the yield is around 71% when the reduction is performed at 160° C. and a pressure of 130 bar. These yields are insufficient for technical processes, and also they can be achieved only when relatively pure phthalic acid anhydride is used. Furthermore, the fact that a relatively high hydrogen pressure must be used is a disadvantage of this method.

The problem therefore existed of performing the catalytic hydrogenation of phthalic acid anhydride to phthalide such that phthalide yields of more than 85% are obtained, even when the hydrogen pressure is less than 100 bar; in addition, technical phthalic acid anhydride is to be usable as starting material without substantial loss of yield.

THE INVENTION

As the solution to this problem, a method has now been found for the preparation of phthalide by catalytic hydrogenation of phthalic acid anhydride with the aid of a nickel catalyst, and it is characterized by performing the hydrogenation in a benzoic acid ester as solvent, with a catalyst of low nickel content.

Preferably, an alkanol, preferably methanol, is used in addition to the benzoic acid ester as solvent.

In the procedure of the invention, phthalide yields far in excess of 75% are obtained. These yields are obtained even when technical phthalic acid anhydride is used as starting material, whereas when it is used in the known hydrogenation processes, even in the presence of alcohols as additional solvents, trouble is encountered in the hydrogenation.

Surprisingly, these improvements of yield are encountered only when benzoic acid esters are used as the solvent. If, for example, the next homologous compounds, for example p-toluylic acid methyl ester, are used as solvents under otherwise analogous conditions, the phthalide yield drops to 53%, and the formation of o-toluylic acid as by-product increases to about 28%.

The nickel content of the catalyst also plays a decisive part in the improvement of the yield over the known methods. The nickel content therefore is to be preferably less than 25%. This refers to the entire catalyst mass, i.e., the catalyst support plus the nickel compound. The catalyst supports in this case are known materials used for supporting nickel catalysts, on which the metallic nickel is firmly fixed. Particularly good results are obtained when the nickel content of the catalyst is between 10 and 15%; however, catalysts having a nickel content as low as 5% can also be used in accordance with the invention.

Of the benzoic acid alkyl esters which can be used as solvents, preference is given to benzoic acid methyl ester. However, the next higher alkyl esters whose ester component contains up to 4 carbon atoms can also be used. These esters are then used preferably with the alcohols corresponding to the ester component.

If in addition to the benzoic acid ester an alkanol is used as solvent for the method of the invention, the latter can be present in amounts of up to 50% of the volume of the benzoic acid ester. In general, the alkanol content is between 5 and 15% of the volume of the benzoic acid ester. The preferred alcohol is methyl alcohol, especially when benzoic acid methyl ester is used as the solvent.

The hydrogen pressure necessary for the reaction in accordance with the invention is surprisingly low. When benzoic acid methyl ester is used with low proportions of methanol and the named nickel catalysts, it is possible to achieve a quantitative transformation of phthalic acid anhydride with a hydrogen pressure of 10 to 50 bar, preferably of 30 bar. In general, a hydrogen pressure up to 80 bar will suffice for a quantitative transformation of the phthalic acid anhydride.

The most favorable temperature range for the procedure of the invention is between 130° and 180° C., preferably between 140° and 160° C.

The acid by-products which occur in small amounts in the process of the invention, such as benzoic acid, orthotoluylic acid, phthalic acid and phthalic acid monomethyl ester, can be removed by an alkaline treatment in a known manner. The phthalide purified in this manner has a melting point of 74° to 76.5° C. and a purity, determined by gas chromatographic analysis, of 96 to 98%.

Phthalide is a valuable chemical intermediate for the preparation of dyes, plant protectants and medicinal products.

EXAMPLES

Example 1

A 20-liter autoclave with a lifting magnetic stirrer is filled under nitrogen with 5.92 kg of phthalic acid anhydride (40 moles), 5 liters of benzoic acid methyl ester, 0.6 kg of methanol and 0.5 kg of nickel catalyst having a nickel content of 12% (commercial product RCH 12/10 of Farbwerke Hoechst). After establishing a hydrogen pressure of 30 bar, the mixture is heated to 150° C. and at this temperature the consumption of hydrogen in the range between 15 and 30 bar is compensated by the addition of more hydrogen for a period of 5 hours. After the pressure becomes constant, the reaction is allowed to continue for another 15 minutes. The mixture obtained is then cooled to 100° C., the pressure is relieved, and the catalyst is removed by filtration; the catalyst was washed with about 3 liters of hot benzoic acid methyl ester. The filtrate was concentrated by evaporation, in a vacuum at the end, to a temperature in the liquid of 160° C. at about 40 mbar.

The residue obtained, with a weight of 5.3 kg and a phthalide content of 89.5% by weight, was refluxed for 15 minutes with 2.6 liters of methanol and 1.05 kg of 25% aqueous ammonia to remove the acid by-products, and then 8 liters of water were added, with cooling and stirring. The phthalide that was thus precipitated was removed by filtration at room temperature, washed with about 1 liter of water, and dried at 55° to 60° C. and 20 mbar. 4.57 kg of phthalide was obtained, with a melting point of 74° to 76.5° C. (GC purity 98.3%), corresponding to 85.3% of the theory.

Example 2

296 g of phthalic acid anhydride was hydrogenated in 250 ml of benzoic acid methyl ester in the presence of 35 g of methanol, in the manner described in Example 1, using 40 g of the nickel catalyst therein described. The reaction conditions and yields are shown in Table 1.

Examples 3 and 4 (For comparison purposes)

In the manner described in Example 2, the same amounts of phthalic acid anhydride were hydrogenated in the same amount of solvent, except that in the one case (Example 3) the nickel content of the catalyst was about 55%, and in the second case (Example 4), p-toluylic acid methyl ester was used instead of benzoic acid methyl ester. In both cases the content of the undesirable o-toluylic acid greatly increased, and the content of other by-products such as phthalic acid and phthalic acid monomethyl ester was twice as high as in the procedure of the invention.

TABLE 1

| Example | 2 | 3 | 4 |
| --- | --- | --- | --- |
| Solvent | BME | BME | PTE[1] |
| Nickel content of the catalyst (%) | 12 | 55 | 12 |
| Reaction conditions | | | |
| Pressure (bar) | 50 | 50 | 50 |
| Temperature (°C.) | 142 | 148 | 149 |
| Time (h) | 5.5 | 2.5 | 6.0 |
| Composition of the reaction product (%) | | | |
| (a) phthalide | 84.6 | 59.2 | 53.1 |
| (b) o-toluylic acid | 10.5 | 27.5 | 28.3 |
| (c) benzoic acid | 1.7 | 1.4 | — |
| (d) phthalic acid + phthalic acid methyl ester | 2.5 | 6.2 | 5.3 |
| (e) other by-products | 0.7 | 5.7 | 13.3 |

[1]PTE = p-toluylic acid methyl ester

It will be understood that the specification and examples are illustrative but not limitative of the present invention and that other embodiments within the spirit and scope of the invention will suggest themselves to those skilled in the art.

What is claimed is:

1. In a method of preparing phthalide by the catalytic hydrogenation of phthalic acid anhydride using a nickel catalyst fixed on a support material, the improvement comprising:
   hydrogenating the anhydride in a benzoic acid ester solvent with an alkanol added thereto and using a nickel catalyst having about 5% to 25% nickel content, said ester being an alkyl ester having up to 4 carbon atoms and having the same number of carbon atoms as the alkanol.

2. The method of claim 1 wherein the nickel content is between 10% and 15%.

3. The method of claim 1 wherein benzoic acid methyl ester is used.

4. The method of claim 3 wherein methanol is the alkanol added to the ester.

5. The method of claim 1 wherein the hydrogenation step further comprises adding 5 to 15% by volume based on the volume of benzoic acid ester solvent of an alkanol to the solvent.

6. The method of claim 1 further comprising maintaining the hydrogenation reaction temperatures at from about 130° C. to about 180° C.

7. The method of claim 6 wherein the temperature ranges from about 140° C. to about 160° C.

8. The method of claim 1 further comprising maintaining the hydrogenation reaction pressure in the range of about 10 to 80 bar of hydrogen pressure.

9. The method of claim 8 wherein the pressure is maintained between 30 to 50 bar of hydrogen pressure.

10. The method of claim 8 wherein about 30 bar of hydrogen pressure is maintained.

11. The method of claim 1 wherein the nickel catalyst has a nickel content from about 5% to about 25%, said benzoic acid ester solvent is an alkyl ester whose ester component contains up to 4 carbon atoms, and further comprising maintaining a temperature of about 130° C. to about 180° C. and a hydrogen pressure of about 10 to 80 bar; and adding 5 to 15% by volume based on the benzoic acid ester solvent, of an alkanol having the same number of carbon atoms as said ester component, to the solvent.

12. The method of claim 11 wherein benzoic acid methyl ester is used as the solvent and is mixed with methanol as the alkanol.

* * * * *